(12) United States Patent
Weeratunga et al.

(10) Patent No.: US 7,375,233 B2
(45) Date of Patent: May 20, 2008

(54) PROCESS FOR THE PREPARATION OF ZONISAMIDE AND THE INTERMEDIATES THEREOF

(75) Inventors: Gamini Weeratunga, Brantford (CA); Eckardt C. G. Wolf, Brantford (CA); Nageib Mohamed, Oakville (CA); Allan W. Rey, Brantford (CA); Bhaskar Reddy Guntoori, Brantford (CA)

(73) Assignee: Apotex Pharmachem Inc., Brantford, Ontario (CA)

( * ) Notice: Subject to any disclaimer, the term of this patent is extended or adjusted under 35 U.S.C. 154(b) by 0 days.

(21) Appl. No.: 11/304,563

(22) Filed: Dec. 16, 2005

(65) Prior Publication Data

US 2007/0142644 A1 Jun. 21, 2007

(51) Int. Cl.
*C07D 261/20* (2006.01)
(52) U.S. Cl. .................................................. 548/241
(58) Field of Classification Search ................ 548/241
See application file for complete search history.

(56) References Cited

U.S. PATENT DOCUMENTS

| 4,172,896 A | 10/1979 | Uno et al. |
| 2002/0183525 A1 | 12/2002 | Mendelovici et al. |

FOREIGN PATENT DOCUMENTS

| JP | 53-77057 A2 | 7/1978 |
| WO | WO 02/070495 A1 | 9/2002 |
| WO | WO 03/020708 A1 | 3/2003 |
| WO | WO 03/072552 A1 | 9/2003 |

OTHER PUBLICATIONS

Casini et al., On 1,2-Benzisoxazole-3-acetic Acid, Journal of Heterocyclic Chemistry, 1965, vol. 2, No. 4, pp. 385-386.
Giannella et al., Aminoacids with 1,2-benzisoxazole nucleus: D,L-(1,2-benzisoxazole-3) glycine, . . . , Chimie Therapeutique, 1972, vol. 7, No. 2, pp. 127-132.
Mustafa et al., Experiments with Substituted (3,2-c)-Pyranyl-2, 10-Diones and Benzopyranyl-(3,2-c) Pyran-2,8-Diones, Tetrahedron, 1963, vol. 19, No. 11, pp. 1831-1839.
Posner, T., Uber die Einwirkung von freiem Hydroxylamin auf Cumarine, Chem. Ber., 1909, 42, pp. 2523-2532.
Uno, H. and Kurokawa, M., Studies on 3-Substituted 1,2-Benzisoxazole Derivatives. V. Electrophilic Substitutions . . . , Chem. Pharm. Bull., 1978, vol. 26, No. 11, pp. 3498-3503.
Uno et al., Studies on 3-Substituted 1,2-Benzisoxazole Derivatives. 6. Syntheses of 3-(Sulfamoylmethyl) . . . , J. Med Chem., 1979, vol. 22, No. 2, pp. 180-183.

*Primary Examiner*—Rei-tsang Shiao
(74) *Attorney, Agent, or Firm*—Ivor M. Hughes; Marcelo K. Sarkis; Kitt Sinden

(57) ABSTRACT

The present invention provides a novel and improved process for the preparation of Zonisamide and the intermediates thereof. In one aspect of the present invention, the process provides for: the preparation and isolation of a novel crystalline form of anhydrous 1,2-benzisoxazole-3-methanesulfonic acid of formula 1; the direct chlorination of the acid of formula 1 into its acid chloride of formula 2; and the in situ conversion of the intermediate acid chloride of formula 2 into Zonisamide

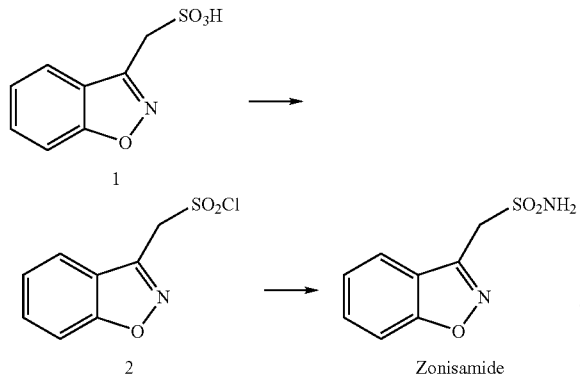

21 Claims, 1 Drawing Sheet

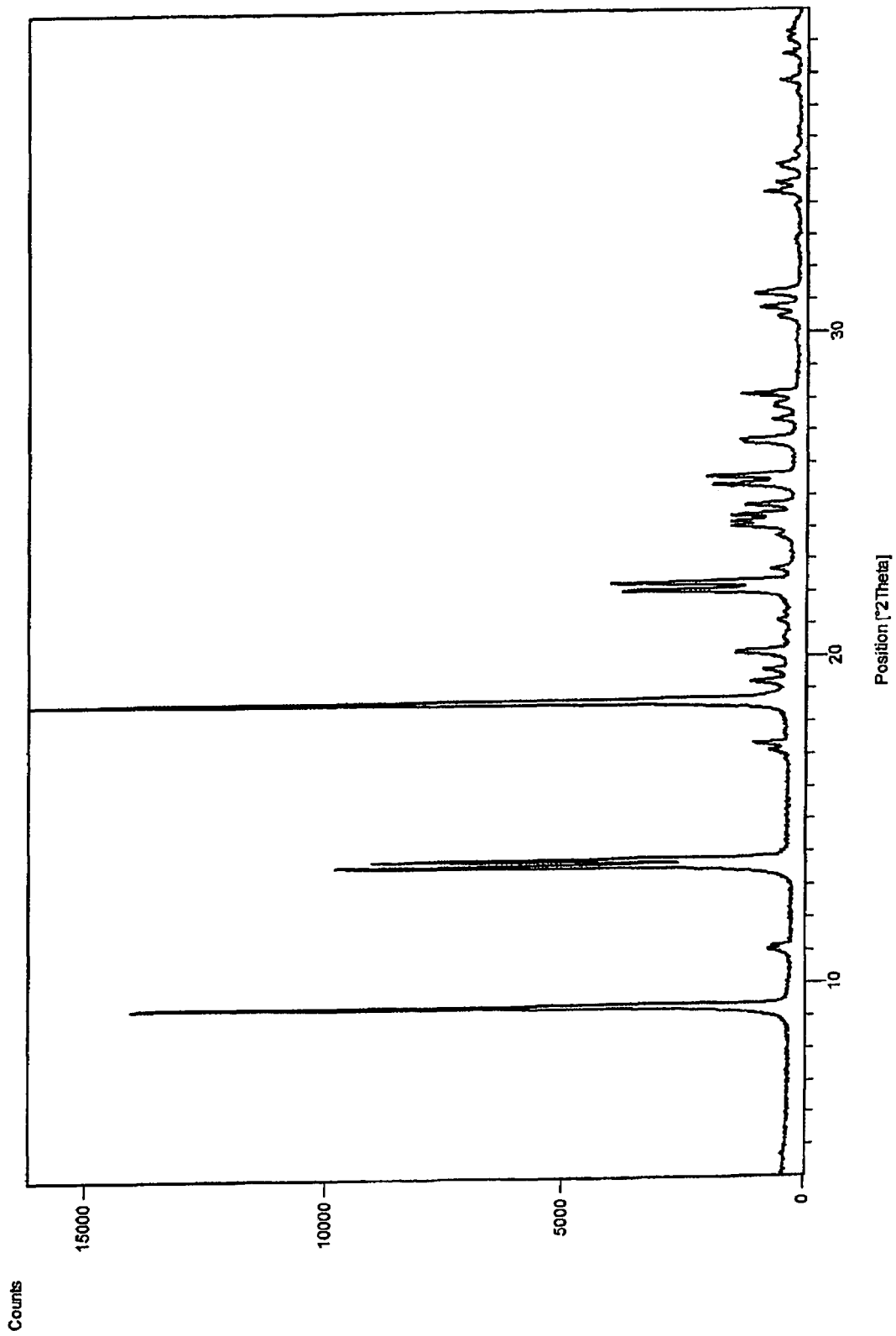
Figure 1 – PXRD Diffractogram of 1,2-Benzisoxazole-3-methanesulfonic acid

PROCESS FOR THE PREPARATION OF ZONISAMIDE AND THE INTERMEDIATES THEREOF

FIELD OF THE INVENTION

The present invention relates to a novel and improved process for the preparation of zonisamide and the intermediates thereof. In particular, the present invention relates to a process for the preparation of zonisamide via a novel crystalline form of anhydrous 1,2-benzisoxazole-3-methanesulfonic acid, a novel chlorination procedure to generate the 1,2-benzisoxazole-3-methanesulfonyl chloride and a subsequent novel amidation procedure.

BACKGROUND OF THE INVENTION

Zonisamide is known as 1,2-benzisoxazole-3-methanesulfonamide or 3-(sulfamoylmethyl)-1,2-benzisoxazole and has anti-convulsant as well as anti-neurotic effects. It is marketed as an anti-epileptic drug (ZONEGRAN™).

The synthesis of zonisamide has been achieved by several routes, most of which begin by the conversion of 4-hydroxycoumarin into 1,2-benzisoxazole-3-acetic acid.

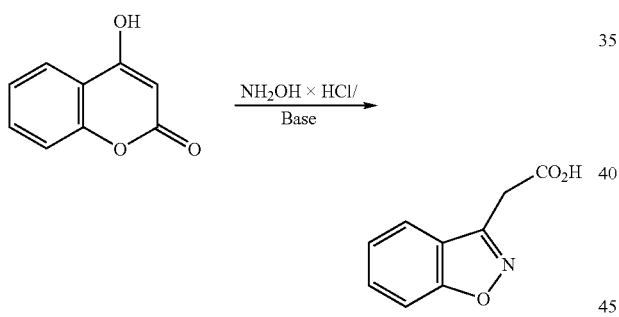

A variety of bases have been used in this reaction including sodium methoxide (generated in situ from sodium metal and methanol; T. Posner, *Chem. Ber.*, 42, 1909, 2523), pyridine (Mustafa et al., *Tetrahedron*, 19, 1963, 1831), sodium acetate (Casini et al., *J. Heterocyclic Chem.*, 1965, 385), alkali carbonates and aliphatic amines (United States Patent Application Publication No. US 2002/0183525 A1 and International Patent Application Publication No. WO 02/0705495 A14).

Two routes have been utilized to convert the 1,2-benzisoxazole-3-acetic acid intermediate into zonisamide. Scheme 2 depicts the initial route for its preparation by a bromination, decarboxylation and nucleophilic substitution sequence to give sodium 1,2-benzisoxazole-3-methanesulfonate (Gianella et al., *Chimie Therapeutique*, 7(2), 1972, 127; and Uno et al., *J. Med Chem.*, 22(2), 1979, 180). This process provides zonisamide in ca. 44% overall yield.

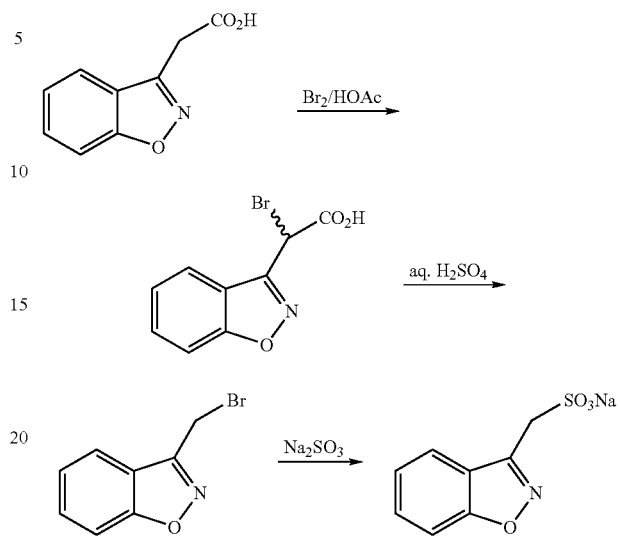

Disadvantages of this process include the fact that the 1,2-benzisoxazole-3-methylbromide intermediate is a strong lachrymator and therefore it is undesirable to handle, especially on scale-up. Also, this intermediate is not very crystalline and tends to separate as an oil before solidifying thereby leading to difficulties with respect to isolation and purification.

Scheme 3 shows the second route by forming sodium 1,2-benzisoxazole-3-methanesulfonate via sulfonization of 1,2-benzisoxazole-3-acetic acid to 1,2-benzisoxazole-3-methanesulfonic acid (1).

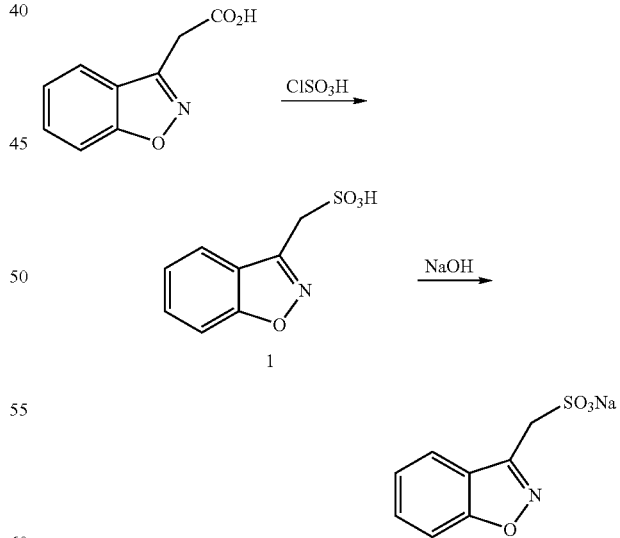

Originally the chlorosulfonization was carried out using excess chlorosulfonic acid as a solvent (H. Uno and M. Kurokawa, *Chem. Pharm. Bull*, 26(11), 1978, 3498). Besides undesired ecological and safety issues that the extremely corrosive chlorosulfonic acid poses, disulfonization occurs. The removal of disulfonated product needs additional purification steps which results in loss of material and costs time, solvent and labour, etc. Later it was discovered that the use of 1,4-dioxane moderates the reactivity of chlorosulfonic acid thereby minimizing concomitant side reactions (U.S. Pat. No. 4,172,896). However, to achieve this, the reaction was carried out in 1,2-dichloroethane, which is a cancer suspect agent. This solvent poses other safety and environmental problems due to its flammability and effects on the ozone layer, respectively.

International Patent Application Publication No. WO 03/020708 A1 discloses the chlorination of sodium 1,2-benzisoxazole-3-methanesulfonate with a very large excess of phosphorous oxychloride ($POCl_3$) to form 1,2-benzisoxazole-3-methanesulfonyl chloride (2) which is isolated and subsequently converted to zonisamide by treatment with ammonia gas (Scheme 4).

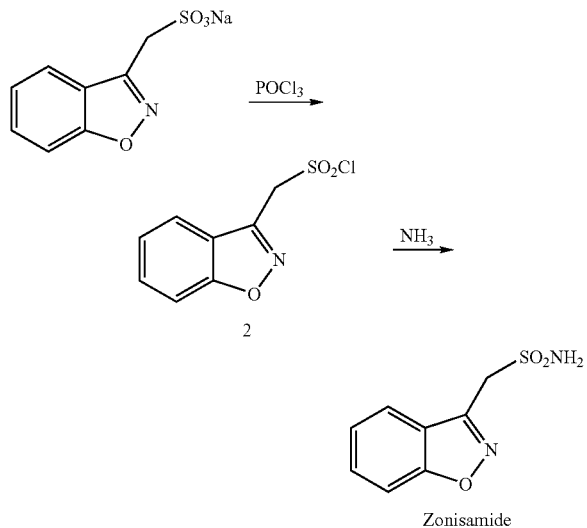

Scheme 4

The disadvantage of this process is that the very large excess of $POCl_3$ (8.1 mol equivalents) must be removed before isolation of 1,2-benzisoxazole-3-methanesulfonyl chloride (2) and subsequent conversion to zonisamide. Direct chlorination of 1,2-benzisoxazole-3-methanesulfonic acid (1) into 1,2-benzisoxazole-3-methanesulfonyl chloride (2) is not described in WO 03/020708. In fact, WO 03/020708 teaches that since 1,2-benzisoxazole-3-methanesulfonic acid (1) is a more hygroscopic compound than its alkaline or earth alkaline salts, it is recommended to isolate the product as a salt rather than the free sulfonic acid. Further, it is taught in WO 03/020708 that due to differences in their solubilities, it is preferable to convert the 1,2-benzisoxazole-3-methanesulfonic acid (1) into its salts for easier separation from the reaction mixture. WO 03/020708 also discloses a 1,2-benzisoxazole-3-methansulfonic acid monohydrate Form I having a water content of about 7.6% (measured by Karl Fischer titration). A 1,2-benzisoxazole-3-methanesulfonic acid (1) having a lower water content of 2.8% (measured by Karl Fischer titration) was obtained from the monohydrate but only after drying under very harsh conditions (drying for two days at 60° C. and for approximately 16 hours at 100° C.), and no further details about the compound are provided in WO 03/020708.

In Japanese unexamined (Kokai) Patent Application No. JP53077057 A2, there is mention of converting a 3-methanesulfonic acid of the general formula (VII)

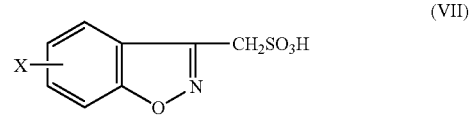

(VII)

directly into a methanesulfonic acid halide of the general formula (II)

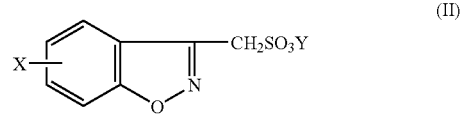

(II)

using a halogenating agent, wherein X is a hydrogen atom or a 5-or 6-position halogen atom and Y indicates a halogen atom, but no further details about the 3-methanesulfonic acid (VII) have been given.

International Patent Application Publication No. WO 03/072552 A1 discloses the conversion of sodium 1,2-benzisoxazole-3-methanesulfonate into 1,2-benzisoxazole-3-methanesulfonyl chloride (2) using thionyl chloride and catalytic amounts of N,N-dimethylformamide (DMF). Although the conversion of 1,2-benzisoxazole-3-methanesulfonic acid (1) to the corresponding 1,2-benzisoxazole-3-methanesulfonyl chloride (2) is generally mentioned in this application, experimental details have only been given for the conversion of the sodium 1,2-benzisoxazole-3-methanesulfonate and, again, large excesses of highly corrosive chlorinating agents were used.

Clearly, an industrial process overcoming the deficiencies of the prior art processes, which would provide zonisamide in a high-yield, cost-effective, environmentally friendlier and safe manner was required.

None of the prior art has characterized the existence of any crystalline forms of anhydrous 1,2-benzisoxazole-3-methanesulfonic acid. There is a continuing need to investigate crystalline forms of 1,2-benzisoxazole-3-methanesulfonic acid which can provide useful intermediates for zonisamide synthesis.

SUMMARY OF THE INVENTION

It is an object of the present invention to provide a new and improved process for the preparation of zonisamide that overcomes the disadvantages of the prior art processes.

It is another object of the present invention to provide a novel crystalline form of anhydrous 1,2-benzisoxazole-3-methanesulfonic acid and a method for its preparation, which sulfonic acid type compound is useful as an intermediate in a process for the preparation of zonisamide.

It is a further object of the present invention to provide a new process for the preparation of 1,2-benzisoxazole-3-methanesulfonyl chloride which process involves the direct chlorination of the novel crystalline form of anhydrous 1,2-benzisoxazole-3-methanesulfonic acid with at least one chlorinating agent.

It is still a further object of the present invention to provide a new process for the preparation of zonisamide which involves the in situ amidation of 1,2-benzisoxazole-3-methanesulfonyl chloride with at least one amidating agent.

Further and other objects of the present invention will be realized by those skilled in the art from the following summary of the invention and detailed description of embodiments thereof.

Through investigations in our laboratory we have found that the product of sulfonating 1,2-benzisoxazole-3-acetic acid may be isolated as the sulfonic acid type compound, namely 1,2-benzisoxazole-3-methanesulfonic acid, in a crystalline anhydrous form with a water content of less than about 2%.

In accordance with one aspect of the present invention, there is provided a crystalline form of anhydrous 1,2-benzisoxazole-3-methanesulfonic acid.

In an embodiment of the present invention, the crystalline form of anhydrous 1,2-benzisoxazole-3-methanesulfonic acid is characterized by an X-Ray powder diffraction (XRPD) having the most characteristic peaks at about 9.32±0.2, 13.59±0.2, 13.78±0.2, 18.64±0.2, 22.03±0.2, 22.27±0.2, 25.31±0.2 and 25.56±0.2 degrees two theta.

In another embodiment of the present invention, the crystalline form of anhydrous 1,2-benzisoxazole-3-methanesulfonic acid has a water content of less than about 2.0%, preferably about 0.8% to about 1.5%.

In accordance with another aspect of the present invention, there is provided a process for preparing a crystalline form of anhydrous 1,2-benzisoxazole-3-methanesulfonic acid, said process comprising the steps of:
  (i) preparing 1,2-benzisoxazole-3-methanesulfonic acid in a reaction mixture;
  (ii) adding at least one anti-solvent to the mixture from step (a) to precipitate the crystalline form of anhydrous 1,2-benzisoxazole-3-methanesulfonic acid; and
  (iii) isolating the crystalline form of anhydrous 1,2-benzisoxazole-3-methanesulfonic acid.

In an embodiment of the present invention, the 1,2-benzisoxazole-3-methanesulfonic acid is prepared by sulfonating 1,2-benzisoxazole-3-acetic acid using chlorosulfonic acid in at least one aprotic organic solvent.

In another embodiment of the present invention, the sulfonation of 1,2-benzisoxazole-3-acetic acid comprises the steps of:
  (a) preparing a mixture of 1,2-benzisoxazole-3-acetic acid and at least one aprotic organic solvent;
  (b) adding chlorosulfonic acid to the mixture from step (a); and
  (c) heating the mixture from step (b).

In another embodiment of the present invention, the at least one aprotic organic solvent is selected from the group consisting of $C_1$-$C_3$ chlorinated solvents and $C_4$-$C_6$ cyclic ethers. The $C_1$-$C_3$ chlorinated solvents may be selected from the group consisting of dichloromethane and dichloroethane and the $C_4$-$C_6$ cyclic ethers may be selected from the group consisting of tetrahydrofuran and 1,4-dioxane. In a preferred embodiment of the present invention, the at least one aprotic organic solvent is 1,4-dioxane.

In another embodiment of the present invention, the chlorosulfonic acid is added to the mixture from step (a) in a molar ratio of 1,2-benzisoxazole-3-acetic acid:chlorosulfonic acid of about 1:1.1.

In another embodiment of the present invention, the mixture from step (b) is heated to a temperature of about 0° C. to about 100° C. and preferably about 20° C. to about 80° C.

In another embodiment of the present invention, the at least one anti-solvent is selected from the group consisting of $C_6$-$C_9$ aromatic hydrocarbons, $C_5$-$C_{10}$ aliphatic hydrocarbons, and $C_1$-$C_3$ halogenated hydrocarbons. The $C_6$-$C_9$ aromatic hydrocarbons may be selected from the group consisting of benzene, toluene, and xylenes; the $C_5$-$C_{10}$ aliphatic hydrocarbons may be selected from the group consisting of hexanes, heptanes, and octanes; and the $C_1$-$C_3$ halogenated hydrocarbons may be selected from the group consisting of dichloromethane and dichloroethane. In a preferred embodiment of the present invention, the at least one anti-solvent is xylenes.

In another embodiment of the present invention, the crystalline form of anhydrous 1,2-benzisoxazole-3-methanesulfonic acid is isolated by filtration under an inert atmosphere and exclusion of moisture.

In another embodiment of the present invention, the crystalline form of anhydrous 1,2-benzisoxazole-3-methanesulfonic acid is thereafter converted to 1,2-benzisoxazole-3-methanesulfonyl chloride.

In another embodiment of the present invention, the crystalline form of anhydrous 1,2-benzisoxazole-3-methanesulfonic acid is thereafter converted to zonisamide.

In accordance with another aspect of the present invention, there is provided a process for the preparation of 1,2-benzisoxazole-3-methanesulfonyl chloride, said process comprising the steps of:
  (a) preparing and subsequently isolating a crystalline form of anhydrous 1,2-benzisoxazole-3-methanesulfonic acid; and
  (b) directly chlorinating the crystalline form of anhydrous 1,2-benzisoxazole-3-methanesulfonic acid obtained in step (a) with at least one chlorinating agent to form 1,2-benzisoxazole-3-methanesulfonyl chloride.

In accordance with another aspect of the present invention, there is provided a process for the preparation of zonisamide, said process comprising the steps of:
  (a) preparing and subsequently isolating a crystalline form of anhydrous 1,2-benzisoxazole-3-methanesulfonic acid;
  (b) treating the crystalline form of anhydrous 1,2-benzisoxazole-3-methanesulfonic acid obtained in step (a) with at least one chlorinating agent to form 1,2-benzisoxazole-3-methanesulfonyl chloride;
  (c) treating the 1,2-benzisoxazole-3-methanesulfonyl chloride obtained in step (b) with at least one amidating agent to form zonisamide; and
  (d) isolating the zonisamide formed in step (c).

In an embodiment of the present invention, the amount of the at least one chlorinating agent used to treat 1,2-benzisoxazole-3-methanesulfonic acid to form 1,2-benzisoxazole-3-methanesulfonyl chloride is about 0.5 to about 5 mol eq relative to the crystalline form of anhydrous 1,2-benzisoxazole-3-methanesulfonic acid.

In another embodiment of the present invention, the at least one chlorinating agent used to treat 1,2-benzisoxazole-3-methanesulfonic acid to form 1,2-benzisoxazole-3-methanesulfonyl chloride may be selected from the group consisting of oxalyl chloride, phosphorus pentachloride, and phosphorus oxychloride. In a preferred embodiment of the present invention, the at least one chlorinating agent used to treat 1,2-benzisoxazole-3-methanesulfonic acid to form 1,2-benzisoxazole-3-methanesulfonyl chloride is phosphorus oxychloride.

In another embodiment of the present invention, the step of treating the 1,2-benzisoxazole-3-methanesulfonic acid with the at least one chlorinating agent to form 1,2-benzisoxazole-3-methanesulfonyl chloride is carried out neat.

In another embodiment of the present invention, the step of treating the 1,2-benzisoxazole-3-methanesulfonic acid with the at least one chlorinating agent to form 1,2-benzisoxazole-3-methanesulfonyl chloride is carried out in the presence of at least one aprotic organic solvent. The at least one aprotic organic solvent may be selected from the group consisting of $C_2$-$C_4$ nitriles, $C_6$-$C_9$ aromatic hydrocarbons, $C_3$-$C_{10}$ acyclic or cyclic ethers, $C_3$-$C_6$ ketones, $C_2$-$C_7$ esters, $C_5$-$C_{10}$ aliphatic hydrocarbons; $C_1$ to $C_3$ chlorinated solvents and combinations thereof. The $C_2$-$C_4$ nitriles may be selected from the group consisting of acetonitrile and propionitrile; the $C_6$-$C_9$ aromatic hydrocarbons may be selected from the group consisting of benzene, toluene, and xylenes; the $C_3$-$C_{10}$ acyclic or cyclic ethers may be selected from the group consisting of dimethoxyethane, diethyl ether, diisopropyl ether, and tetrahydrofuran; the $C_3$-$C_6$ ketones may be selected from the group consisting of methyl isobutyl ketone and methyl ethyl ketone; the $C_2$-$C_7$ esters may be selected from the group consisting of ethyl acetate, ethyl propionate, and isopropyl acetate; the $C_5$-$C_{10}$ aliphatic hydrocarbons may be selected from the group consisting of hexanes, heptanes, and octanes; and the $C_1$ to $C_3$ chlorinated solvents may be selected from the group consisting of dichloromethane and chloroform. In a preferred embodiment of the present invention, the at least one aprotic organic solvent is acetonitrile. In another preferred embodiment of the present invention, the at least one aprotic organic solvent is xylenes.

In another embodiment of the present invention, the step of treating the 1,2-benzisoxazole-3-methanesulfonic acid with the at least one chlorinating agent to form 1,2-benzisoxazole-3-methanesulfonyl chloride is carried out at a temperature of about 50° C. to about 160° C., preferably about 50° C. to about 140° C. and more preferably about 50° C. to about 85° C.

In another embodiment of the present invention, the step of treating the 1,2-benzisoxazole-3-methanesulfonyl chloride with the at least one amidating agent to form zonisamide is carried out in situ.

In another embodiment of the present invention, prior to the step of treating the 1,2-benzisoxazole-3-methanesulfonyl chloride with the at least one amidating agent, the 1,2-benzisoxazole-3-methanesulfonyl chloride is isolated.

In another embodiment of the present invention, prior to the step of treating the 1,2-benzisoxazole-3-methanesulfonyl chloride with the at least one amidating agent, the 1,2-benzisoxazole-3-methanesulfonyl chloride is isolated from solution in at least one organic solvent.

In another embodiment of the present invention, the at least one organic solvent from which the 1,2-benzisoxazole-3-methanesulfonyl chloride is isolated prior to the step of treating the 1,2-benzisoxazole-3-methanesulfonyl chloride with the at least one amidating agent, is selected from $C_6$-$C_9$ aromatic hydrocarbons and $C_5$-$C_{10}$ aliphatic hydrocarbons. The $C_6$-$C_9$ aromatic hydrocarbons is selected from the group consisting of benzene, toluene and xylenes and the $C_5$-$C_{10}$ aliphatic hydrocarbons may be selected from hexanes, heptanes and octanes. In a preferred embodiment, the at least one organic solvent from which the 1,2-benzisoxazole-3-methanesulfonyl chloride is isolated is xylenes. In another preferred embodiment, the at least one organic solvent from which the 1,2-benzisoxazole-3-methanesulfonyl chloride is isolated is toluene.

In another embodiment of the present invention, prior to the step of treating the 1,2-benzisoxazole-3-methanesulfonyl chloride with the at least one amidating agent, the 1,2-benzisoxazole-3-methanesulfonyl chloride is isolated by evaporation.

In another embodiment of the present invention, the at least one amidating agent used to treat the 1,2-benzisoxazole-3-methanesulfonyl chloride to form zonisamide is selected from the group consisting of aqueous ammonia, masked ammonia and ammonia gas. The masked ammonia may be an ammonium salt selected from the group consisting of ammonium carbonate, ammonium acetate and ammonium formate. The ammonia gas may be anhydrous ammonia gas consisting of less than about 200 ppm water, preferably less than about 20 ppm water. In a preferred embodiment of the present invention, the at least one amidating agent is ammonia gas.

In another embodiment of the present invention, the step of treating the 1,2-benzisoxazole-3-methanesulfonyl chloride with the at least one amidating agent is carried out in the presence of at least one organic solvent. The at least one organic solvent may be selected from the group consisting of $C_3$-$C_6$ ketones and $C_2$-$C_7$ esters. The $C_3$-$C_6$ ketones may be selected from the group consisting of methyl isobutyl ketone and methyl ethyl ketone. The $C_2$-$C_7$ esters may be selected from the group consisting of ethyl acetate, ethyl propionate, and isopropyl acetate. In a preferred embodiment of the present invention, the at least one organic solvent is ethyl acetate.

In another embodiment of the present invention, the step of treating the 1,2-benzisoxazole-3-methanesulfonyl chloride with the at least one amidating agent to form zonisamide is carried out at a temperature of about −50° C. to about 50° C. and preferably about −10° C. to about 30° C.

In accordance with another aspect of the present invention there is provided a process for the preparation of zonisamide, said process comprising the steps of:
  (a) reacting 1,2-benzisoxazole-3-acetic acid with chlorosulfonic acid to form 1,2-benzisoxazole-3-methanesulfonic acid;
  (b) treating the 1,2-benzisoxazole-3-methanesulfonic acid obtained in step (a) with at least one chlorinating agent to form 1,2-benzisoxazole-3-methanesulfonyl chloride; and
  (c) treating the 1,2-benzisoxazole-3-methanesulfonyl chloride obtained in step (b) with at least one amidating agent to form zonisamide in situ.

In accordance with another aspect of the present invention there is provided a process for the preparation of zonisamide, said process comprising the steps of:
  (a) reacting 1,2-benzisoxazole-3-acetic acid with chlorosulfonic acid to form 1,2-benzisoxazole-3-methanesulfonic acid;
  (b) adding at least one anti-solvent to the mixture from step (a) to precipitate the 1,2-benzisoxazole-3-methanesulfonic acid in a crystalline anhydrous form;
  (c) isolating the crystalline form of anhydrous 1,2-benzisoxazole-3-methanesulfonic acid obtained in step (b);
  (d) treating the crystalline form of anhydrous 1,2-benzisoxazole-3-methanesulfonic acid isolated in step (c) with at least one chlorinating agent to form 1,2-benzisoxazole-3-methanesulfonyl chloride; and
  (e) treating the 1,2-benzisoxazole-3-methanesulfonyl chloride obtained in step (d) with at least one amidating agent to form zonisamide.

In accordance with another aspect of the present invention, there is provided a process for the preparation of zonisamide, said process comprising the steps of:

(a) preparing a crystalline form of anhydrous 1,2-benzisoxazole-3-methanesulfonic acid;
(b) directly chlorinating the crystalline form of anhydrous 1,2-benzisoxazole-3-methanesulfonic acid obtained in step (a) with at least one chlorinating agent to form 1,2-benzisoxazole-3-methanesulfonyl chloride; and
(c) treating the 1,2-benzisoxazole-3-methanesulfonyl chloride obtained in step (b) with at least one amidating agent to form zonisamide in situ.

In accordance with another aspect of the present invention, there is provided a process for the preparation of zonisamide, said process comprising the steps of:
(a) preparing a crystalline form of anhydrous 1,2-benzisoxazole-3-methanesulfonic acid;
(b) reacting the crystalline form of anhydrous 1,2-benzisoxazole-3-methanesulfonic acid obtained in step (a) with at least one chlorinating agent neat or in the presence of at least one organic solvent to form 1,2-benzisoxazole-3-methanesulfonyl chloride; and
(c) reacting the 1,2-benzisoxazole-3-methanesulfonyl chloride obtained in step (b) without isolation with ammonia gas in the presence of at least one organic solvent.

In accordance with another aspect of the present invention, there is provided a process for the preparation of zonisamide, said process comprising the steps of:
(a) reacting 1,2-benzisoxazole-3-acetic acid with chlorosulfonic acid to form 1,2-benzisoxazole-3-methanesulfonic acid;
(b) precipitating the 1,2-benzisoxazole-3-methanesulfonic acid obtained in step (a) in a crystalline anhydrous form by the addition of at least one antisolvent;
(c) converting the crystalline form of anhydrous 1,2-benzisoxazole-3-methanesulfonic acid obtained in step (b) into 1,2-benzisoxazole-3-methanesulfonyl chloride by treatment with at least one chlorinating agent; and
(d) transforming the 1,2-benzisoxazole-3-methanesulfonyl chloride obtained in step (c) in situ into zonisamide by the addition of ammonia.

In accordance with another aspect of the present invention, there is provided a process to convert a crystalline form of anhydrous 1,2-benzisoxazole-3-methanesulfonic acid directly into its corresponding 1,2-benzisoxazole-3-methanesulfonyl chloride.

In accordance with another aspect of the present invention, there is provided a process for preparing 1,2-benzisoxazole-3-methanesulfonyl chloride, said process comprising the steps of:
(a) preparing a crystalline form of anhydrous 1,2-benzisoxazole-3-methanesulfonic acid; and
(b) treating the 1,2-benzisoxazole-3-methanesulfonic acid obtained in step (a) with at least one chlorinating agent to form 1,2-benzisoxazole-3-methanesulfonyl chloride.

In accordance with another aspect of the present invention, there is provided a process for preparing 1,2-benzisoxazole-3-methanesulfonyl chloride, wherein said process comprises the step of chlorinating a crystalline form of anhydrous 1,2-benzisoxazole-3-methanesulfonic acid.

In accordance with another aspect of the present invention, there is provided a process for preparing a crystalline form of anhydrous 1,2-benzisoxazole-3-methanesulfonic acid, said process comprising the steps of preparing 1,2-benzisoxazole-3-methanesulfonic acid in a reaction mixture and adding at least one anti-solvent to the reaction mixture.

In accordance with another aspect of the present invention, there is provided a process for preparing zonisamide, said process comprising the steps of:
(a) preparing 1,2-benzisoxazole-3-methanesulfonyl chloride in a reaction mixture; and
(b) treating the 1,2-benzisoxazole-3-methanesulfonyl chloride obtained in step (a) with at least one amidating agent to form zonisamide in situ.

BRIEF DESCRIPTION OF THE DRAWINGS

The present invention will be further understood from the following description with references to the drawings in which:

FIG. 1 illustrates the X-ray powder diffraction (XRPD) pattern of a novel crystalline form of anhydrous 1,2-benzisoxazole-3-methanesulfonic acid.

DETAILED DESCRIPTION OF THE INVENTION

The present invention relates to a novel process for the preparation of zonisamide, also known as 1,2-benzisoxazole-3-methansulfonamide.

The starting material for use in the process of the present invention is 1,2-benzisoxazole-3-acetic acid. It is prepared according to processes known in the prior art, for instance, processes starting with 4-hydroxycoumarin and hydroxylamine (Casini et al., *J. Heterocyclic Chem.*, 1965, 385).

The novel process of the present invention is based on an easy to scale up procedure involving the sulfonation of 1,2-benzisoxazole-3-acetic acid, direct chlorination of 1,2-benzisoxazole-3-methanesulfonic acid, and subsequent amidation of 1,2-benzisoxazole-3-methanesulfonyl chloride to zonisamide.

The process of the present invention is more efficient than the prior art processes in that it permits isolation of the 1,2-benzisoxazole-3-methanesulfonic acid (1) intermediate from the sulfonating reaction mixture, rather than its salt (for example sodium salt), and direct chlorination of this compound to generate 1,2-benzisoxazole-3-methanesulfonyl chloride. We have found that by judicious choice of the reagents, solvents and reaction conditions, the 1,2-benzisoxazole-3-methanesulfonic acid (1) intermediate can be precipitated directly from the sulfonating reaction mixture by using an anti-solvent. An unexpected advantage of this process is that it provides the 1,2-benzisoxazole-3-methanesulfonic acid (1) intermediate in a crystalline anhydrous form having a low water content (typically equal to or below about 2.0% as measured by Karl Fischer titration). This facilitates the subsequent transformation of the 1,2-benzisoxazole-3-methanesulfonic acid (1) intermediate into the corresponding 1,2-benzisoxazole-3-methanesulfonyl chloride (2) intermediate by treatment with an unexpectedly small excess (ca. 0.7 mol equivalents) of chlorinating agent, for example phosphorous oxychloride. This also facilitates the subsequent in situ transformation of the 1,2-benzisoxazole-3-methanesulfonyl chloride (2) intermediate by amidation into zonisamide in excellent yield (85-90%).

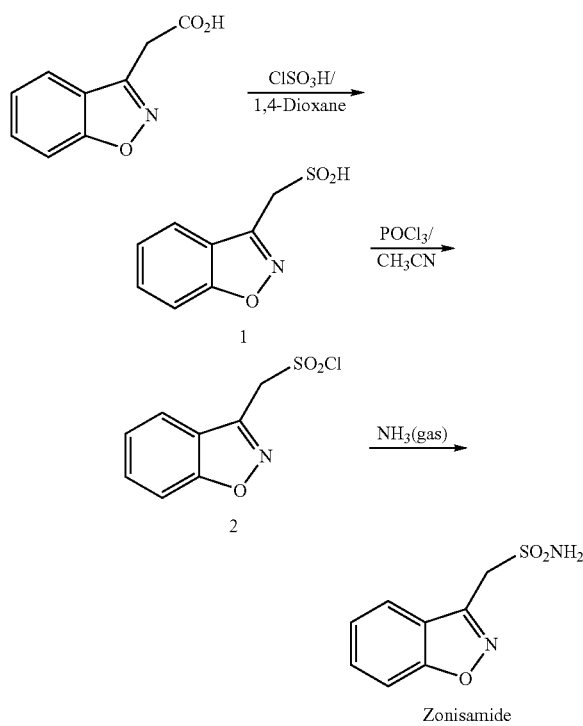

It should be noted that this process reduces the amount of corrosive reagents and increases the over-all yield relative to the prior art processes. This is advantageous in terms of reducing the environmental impact of the process and improving the overall safety.

Further details of the preferred embodiments of the present invention are illustrated in the following examples which are understood to be non-limiting.

EXAMPLE 1

Preparation of Crystalline Anhydrous 1,2-Benzisoxazole-3-methanesulfonic acid (1)

1,2-Benzisoxazole-3-acetic acid (200 g; 1.13 mol) was suspended in 1,4-dioxane (600 mL). The mixture was cooled in an ice-bath and chlorosulfonic acid (82.6 mL, 1.24 mol, 1.1 eq) was added maintaining the internal temperature below 20° C. The mixture was heated to 60-65° C. for 9½ h and cooled to room-temperature. CELITE™ (20 g) was added followed by xylenes (1000 mL) and the mixture was stirred for one hour at room temperature. It was filtered and concentrated. The suspension obtained was heated to 50-60° C. for three hours and then gradually cooled to 0-5° C. and filtered. The precipitate was filtered off under a nitrogen atmosphere and washed with 400 mL 1,4-dioxane/xylenes (v/v=1:9). It was dried at 60° C. for approximately 16 hours in a vacuum oven ($\leq$1 mm Hg) to give 218.14 g crystalline anhydrous 1,2-benzisoxazole-3-methanesulfonic acid (90.6%) with a HPLC purity of 99.4%.

Crystalline anhydrous 1,2-benzisoxazole-3-methanesulfonic acid was characterized as follows:

$^1$H NMR (300 MHz, DMSO-$d_6$): δ (ppm) 10.75 [1H, s (br)], 8.05 (1H, ad, J=8.1 Hz), 7.69 (1H, ad, J=8.6 Hz), 7.62 (1H, at, J=7.7 Hz), 7.37 (1H, at, J=7.3 Hz), 4.28 (2H, s)

$^{13}$C NMR (75 MHz, DMSO-$d_6$): δ (ppm) 162.6, 153.8, 130.2, 124.6, 123.4, 121.7, 109.4, 48.1

LRMS (ES+): 214.2 (100, M+H$^+$)
HRMS: 213.0093 (calculated for $C_8H_7NO_4S$: 213.0096)
XRPD:

The XRPD system was a PANalytical X'Pert Pro MPD theta-theta diffractometer having a X'Celerator high-speed detector and a spinning sample stage. The Radiation source was Copper Kα, and the Power setting was 45 kV and 40 mA. The Step size was 0.08 degrees 2 theta, and the Step time was 6.72 seconds. An Incident beam fixed divergence slit of 0.25 degree was used, along with a fixed anti-scatter slit of 0.5 degrees. The Diffracted beam anti-scatter slit was 5 mm, and the Incident and diffracted beam soller slits were 0.04 rad. The main peaks in the XRPD pattern have the following 2 theta angles at about 9.32±0.2, 13.59±0.2, 13.78±0.2, 17.31±0.2, 18.64±0.2, 19.20±0.2, 20.07±0.2, 20.11±0.2, 22.03±0.2, 22.27±0.2, 24.02±0.2, 24.19±0.2, 24.37±0.2, 24.69±0.2, 25.31±0.2, 25.56±0.2, 26.65±0.2, 28.09±0.2, 30.74±0.2, and 31.17±0.2. The most characteristic peaks in the XRPD pattern have the following 2 theta angles at about 9.32±0.2, 13.59±0.2, 13.78±0.2, 18.64±0.2, 22.03±0.2, 22.27±0.2, 25.31±0.2 and 25.56±0.2. The XRPD pattern is provided in FIG. 1.

KF 0.17% (The water content after 2 years storage was 0.51% as measured by KF. It was determined to be pure by NMR.)

EXAMPLE 2

Preparation of Zonisamide Through Chlorination in Acetonitrile 1,2-Benzisoxazole-3-methanesulfonic acid (1) (20.0 g, 93.8 mmol) was mixed with acetonitrile (60 mL) and heated to reflux. The clear solution was cooled to 65° C. and phosphorous oxychloride (5.7 mL; 62.3 mmol) was added. The mixture was heated to reflux for 10 hours and then cooled to room temperature. Ethyl acetate (100 mL) was added and the mixture was filtered through CELITE™, which was subsequently washed with ethyl acetate (40 mL). The filtrate was cooled in an ice bath and ammonia gas was bubbled through the solution for 1 hour. The mixture was concentrated and water (100 mL) was added. The mixture was heated to reflux and cooled. It was concentrated, cooled in an ice-bath and filtered to yield crude zonisamide. Purification was achieved by recrystallization from iso-propanol/water. The yield of purified product was 78.8%.

It was characterized as follows:

$^1$H NMR (DMSO-$d_6$): δ [ppm] 7.98 (1H, ad, J=7.9 Hz), 7.78 (1H, ad, J=8.5 Hz), 7.68 (1H, at, J=7.7 Hz), 7.44 (1H, at, J=7.4 Hz), 7.27 (2H, s(br)), 4.86 (2H, s)

$^{13}$C NMR (DMSO-$d_6$): δ [ppm] 162.8, 150.8, 130.5, 123.9, 123.3, 121.1, 109.6, 50.9

LRMS (ES$^-$): 211.10 (34, M−H$^+$)
EA: C, 45.12%; (calc. 45.28%); H, 3.70%; (calc. 3.80%); N, 13.00%; (calc. 13.20%)

EXAMPLE 3

Preparation of Zonisamide Through Chlorination in Xylenes 1,2-Benzisoxazole-3-methanesulfonic acid (1) (1.00 g, 4.7 mmol) was mixed with xylenes (10 mL) and phosphorous oxychloride (1.0 mL, 11 mmol) and heated to reflux until the reaction was complete. The mixture was filtered through CELITE™ and evaporated to dryness to yield 1,2-benzisoxazole-3-methanesulfonyl chloride (2) as a light brown solid. It was dissolved in ethyl acetate (10 mL), cooled in an ice-bath and treated with ammonia. Work-up analogous to example 2 gave pure zonisamide.

EXAMPLE 4

Preparation of Zonisamide Through Chlorination in Neat Phosphorous Oxychloride 1,2-Benzisoxazole-3-methanesulfonic acid (1) (2.13 g, 10 mmol) was mixed with phosphorous oxychloride (7 mL, 75 mmol) and refluxed until the reaction was complete. The mixture was diluted with xylenes and concentrated to remove excess phosphorous oxychloride. The mixture was treated as in Example 3 to yield pure zonisamide.

EXAMPLE 5

Preparation of Zonisamide Through Chlorination in Dichloroethane 1,2-Benzisoxazole-3-methanesulfonic acid (1) (1.00 g, 4.7 mmol) was mixed with 1,2-dichloroethane (10 mL) and phosphorous oxychloride (2.0 mL, 21 mmol). The mixture was heated to reflux until the reaction was complete, filtered through CELITE™ and evaporated to give 1,2-benzisoxazole-3-methanesulfonyl chloride (2). It was converted into zonisamide in analogy to the previous examples.

While the foregoing provides a detailed description of preferred embodiments of the present invention, it is to be understood that this description is only illustrative of the principles of the invention and is not limitative. Numerous modifications, variations and adaptations may be made to the particular embodiments of the invention described above without departing from the scope of the invention, which is defined in the claims.

The invention claimed is:

1. A process for the preparation of 1,2-benzisoxazole-3-methanesulfonyl chloride, said process comprising the steps of:
   (a) preparing and subsequently isolating a crystalline form of anhydrous 1,2-benzisoxazole-3-methanesulfonic acid having a water content of less than about 2.0% and
   (b) directly chlorinating the crystalline form of anhydrous 1,2-benzisoxazole-3-methanesulfonic acid obtained in step (a) with at least one chlorinating agent in the presence of at least one aprotic organic solvent to form 1,2-benzisoxazole-3-methanesulfonyl chloride.

2. The process according to claim 1 wherein the amount of the at least one chlorinating agent of step (b) is about 0.5 to about 5 mol equivalents relative to the crystalline form of anhydrous 1,2-benzisoxazole-3-methanesulfonic acid.

3. The process according to claim 1 or 2 wherein the at least one chlorinating agent of step (b) is selected from the group consisting of oxalyl chloride, phosphorus pentachloride, and phosphorus oxychloride.

4. The process according to claim 1 or 2 wherein the at least one chlorinating agent of step (b) is phosphorus oxychloride.

5. The process according to claim 1 or 2 wherein the at least one aprotic organic solvent is selected from the group consisting of $C_2$-$C_4$ nitriles, $C_6$-$C_9$ aromatic hydrocarbons, $C_3$-$C_{10}$ acyclic or cyclic ethers, $C_3$-$C_6$ ketones, $C_2$-$C_7$ esters, $C_5$-$C_{10}$ aliphatic hydrocarbons; $C_1$ to $C_3$ chlorinated solvents and combinations thereof.

6. The process according to claim 3 wherein the at least one aprotic organic solvent is selected from the group consisting of $C_2$-$C_4$ nitriles, $C_6$-$C_9$ aromatic hydrocarbons, $C_3$-$C_{10}$ acyclic or cyclic ethers, $C_3$-$C_6$ ketones, $C_2$-$C_7$ esters, $C_5$-$C_{10}$ aliphatic hydrocarbons; $C_1$ to $C_3$ chlorinated solvents and combinations thereof.

7. The process according to claim 4 wherein the at least one aprotic organic solvent is selected from the group consisting of $C_2$-$C_4$ nitriles, $C_6$-$C_9$ aromatic hydrocarbons, $C_3$-$C_{10}$ acyclic or cyclic ethers, $C_3$-$C_6$ ketones, $C_2$-$C_7$ esters, $C_5$-$C_{10}$ aliphatic hydrocarbons; $C_1$ to $C_3$ chlorinated solvents and combinations thereo 8. The process according to claim 5 wherein the $C_2$-$C_4$ nitriles are selected from the group consisting of acetonitrile and propionitrile; the $C_6$-$C_9$ aromatic hydrocarbons are selected from the group consisting of benzene, toluene, and xylenes; the $C_3$-$C_{10}$ acyclic or cyclic ethers are selected from the group consisting of dimethoxyethane, diethyl ether, diisopropyl ether, and tetrahydrofuran; the $C_3$-$C_6$ ketones are selected from the group consisting of methyl isobutyl ketone and methyl ethyl ketone; the $C_2$-$C_7$ esters are selected from the group consisting of ethyl acetate, ethyl propionate, and isopropyl acetate; the $C_5$-$C_{10}$ aliphatic hydrocarbons are selected from the group consisting of hexanes, heptanes, and octanes; and the $C_1$ to $C_3$ chlorinated solvents are selected from the group consisting of dichloromethane and chloroform.

9. The process according to claim 6 or 7 wherein the $C_2$-$C_4$ nitriles are selected from the group consisting of acetonitrile and propionitrile; the $C_6$-$C_9$ aromatic hydrocarbons are selected from the group consisting of benzene, toluene, and xylenes; the $C_3$-$C_{10}$ acyclic or cyclic ethers are selected from the group consisting of dimethoxyethane, diethyl ether, diisopropyl ether, and tetrahydrofuran; the $C_3$-$C_6$ ketones are selected from the group consisting of methyl isobutyl ketone and methyl ethyl ketone; the $C_2$-$C_7$ esters are selected from the group consisting of ethyl acetate, ethyl propionate, and isopropyl acetate; the $C_5$-$C_{10}$ aliphatic hydrocarbons are selected from the group consisting of hexanes, heptanes, and octanes; and the $C_1$ to $C_3$ chlorinated solvents are selected from the group consisting of dichloromethane and chloroform.

10. The process according to claim 1 or 2 wherein the at least one aprotic organic solvent of step (b) is acetonitrile.

11. The process according to claim 3 wherein the at least one aprotic organic solvent of step (b) is acetonitrile.

12. The process according to claim 4 wherein the at least one aprotic organic solvent of step (b) is acetonitrile.

13. The process according to claim 1 or 2 wherein the at least one aprotic organic solvent of step (b) is xylenes.

14. The process according to claim 3 wherein the at least one aprotic organic solvent of step (b) is xylenes.

15. The process according to claim 4 wherein the at least one aprotic organic solvent of step (b) is xylenes.

16. The process of claim 1 wherein the preparation of the crystalline form of anhydrous 1,2-benzisoxazole-3-methanesutfonic acid comprises the steps of:
   (a) preparing 1,2-benzisoxazole-3-methanesulfonic acid in a reaction mixture and
   (b) adding at least one anti-solvent to the mixture from step (a) to precipitate the crystalline form of anhydrous 1,2-benzisoxazole-3-methanesulfonic acid.

17. The process according to claim 16 wherein the at least one anti-solvent is selected from the group consisting of $C_6$-$C_9$ aromatic hydrocarbons, $C_5$-$C_{10}$ aliphatic hydrocarbons, and $C_1$-$C_3$ halogenated hydrocarbons.

18. The process according to claim 17 wherein the $C_6$-$C_9$ aromatic hydrocarbons are selected from the group consisting of benzene, toluene, and xylenes; the $C_5$-$C_{10}$ aliphatic hydrocarbons are selected from the group consisting of hexanes, heptanes, and octanes; and the $C_1$-$C_3$ halogenated hydrocarbons are selected from the group consisting of dichloromethane and dichloroethane.

19. The process according to claim 16 wherein the at least one anti-solvent is xylenes.

20. The process according to claim 1 wherein the crystalline form of anhydrous 1,2-benzisoxazole-3-methanesulfonic acid has a water content of about 0.8% to about 1.5%.

21. The process according to claim 1 wherein the crystalline form of anhydrous 1,2-benzisoxazole-3-methanesulfonic acid is characterized by an x-ray powder diffraction (XRPD) pattern having the most characteristic peaks at about 9.32±0.2, 13.59±0.2, 13.78±0.2, 18.64±0.2, 22.03±0.2, 22.27±0.2, 25.31±0.2, and 25.56±0.2 degrees two theta.

* * * * *